(12) United States Patent
Ramirez et al.

(10) Patent No.: US 9,187,518 B2
(45) Date of Patent: *Nov. 17, 2015

(54) ANTIANGIOGENIC BRASSINOSTEROID COMPOUNDS

(71) Applicants: CONSEJO NACIONAL DE INVESTIGACIONES CIENTIFICAS Y TECNICAS (CONICET), Buenos Aires (AR); INIS BIOTECH LLC, Mildford, DE (US)

(72) Inventors: Javier Alberto Ramirez, Buenos Aires (AR); Flavia Mariana Michelini, Prov. de Buenos Aires (AR); Lydia Raquel Galagovsky, Buenos Aires (AR); Alejandro Berra, Prov. de Buenos Aires (AR); Laura Edith Alche, Buenos Aires (AR)

(73) Assignees: CONSEJO NACIONAL DE INVESTIGACIONES CIENTIFICAS Y TECNICAS (CONICET), Buenos Aires (AR); INIS BIOTECH LLC, Milford, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/365,893

(22) PCT Filed: Dec. 14, 2012

(86) PCT No.: PCT/IB2012/057325
§ 371 (c)(1),
(2) Date: Jun. 16, 2014

(87) PCT Pub. No.: WO2013/088400
PCT Pub. Date: Jun. 20, 2013

(65) Prior Publication Data
US 2015/0094288 A1 Apr. 2, 2015

(30) Foreign Application Priority Data

Dec. 15, 2011 (AU) .................................. 2011905241

(51) Int. Cl.
*A61K 31/575* (2006.01)
*A61K 45/06* (2006.01)
*C07J 9/00* (2006.01)

(52) U.S. Cl.
CPC .................. *C07J 9/00* (2013.01); *A61K 31/575* (2013.01); *A61K 45/06* (2013.01)

(58) Field of Classification Search
USPC .................................... 514/171, 177; 540/120
See application file for complete search history.

(56) References Cited

FOREIGN PATENT DOCUMENTS

WO WO 2009/007895 1/2009

OTHER PUBLICATIONS

International Search Report, PCT/IB2012/057325, Apr. 4, 2013.
Michelini F M et al: "Anti-herpetic and anti-inflammatory activities of two new synthetic 22,23-dihyroxylated stigmastane derivatives", Journal of Steroid Biochemistry and Molecular Biology, Elsevier Science Ltd., Oxford, GB, vol. 111, No. 1-2, Jul. 1, 2008, pp. 111-116, XP023314538, ISSN: 0960-0760, DOI: 10.1016/J.JSBMB. 2008.05.005 [retrieved on Jul. 10, 2007] the whole document.
Misharin A Yu et al: Toxicity of (22R,23R)—22,23-dihyroxystigmastane derivatives to cultured cancer cells, Steroids, Elsevier Science Publishers, New York, NY US, vol. 75, No. 3, Mar. 1, 2010, pp. 287-294, XP026906107, ISSN: 0039-128X, DOI: 10.1016/J.STEROIDS.2010.01.006 [retrieved on Feb. 12, 2010] the whole document.
Misharin et al: "Synthesis and cytotoxicity evaluation of 22,23-oxygenaged stigmastane derivatives", Bioorganic & Medicinal Chemistry, Pergamon, GB, vol. 16, No. 3, Oct. 22, 2007, pp. 1460-1473, XP022453115, ISSN: 0968-0896, DOI: 10.1016/J.BMC.2007. 10.056 the whole document.

*Primary Examiner* — Shirley V Gembeh
(74) *Attorney, Agent, or Firm* — Young & Thompson

(57) ABSTRACT

A method of treating a solid tumor in a mammal by inhibiting angiogenesis, including administering to the mammal which has a solid tumor selected from the group consisting of breast carcinoma, lung carcinoma, prostate carcinoma, colon carcinoma, ovarian carcinoma, neuroblastoma, central nervous system tumor, multiform glioblastoma and melanoma; a composition including brassinosteroids of general formula (I)

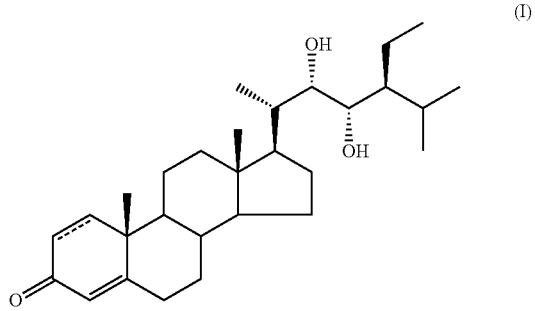

wherein ⌐ can be a single or double bond and the configurations of carbon atoms C22 and C23 respectively linked to the substituents HO are S for both carbon atoms and a pharmaceutically acceptable additive.

12 Claims, 7 Drawing Sheets

Figure 3
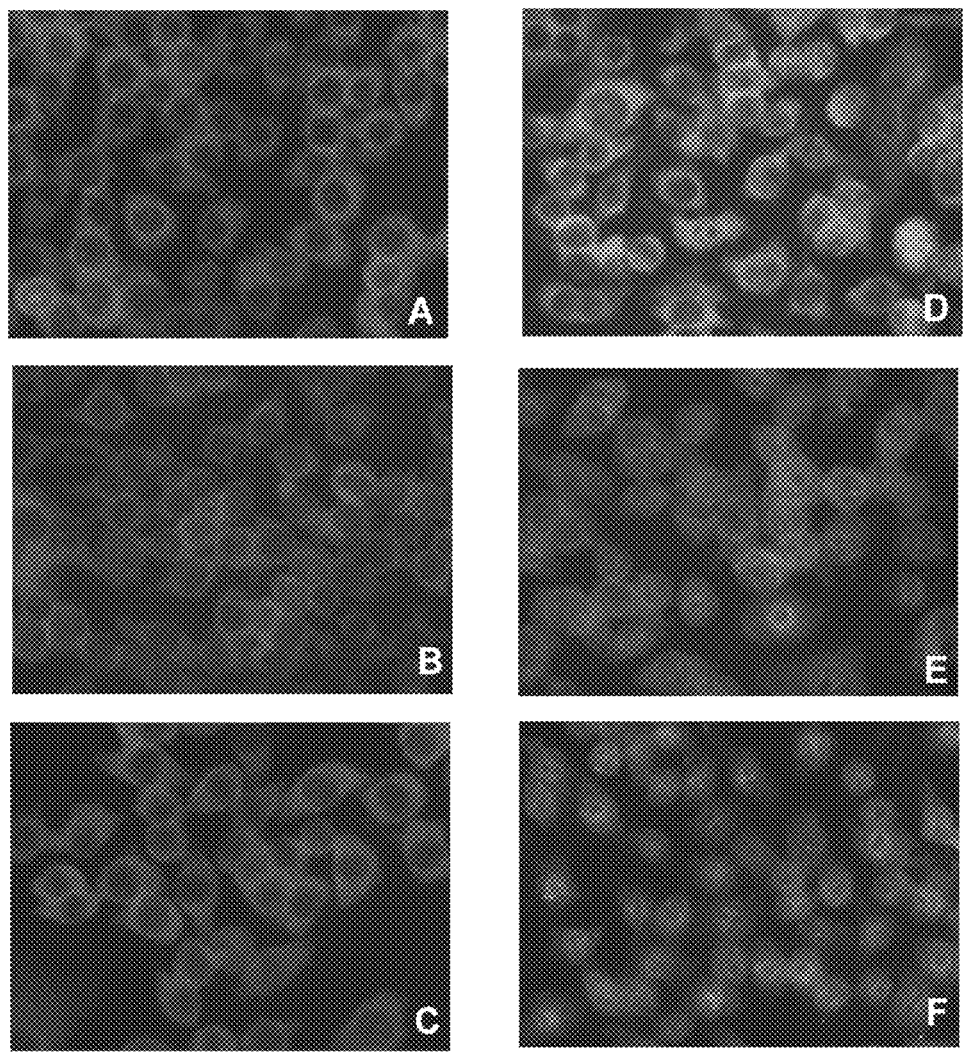
G)
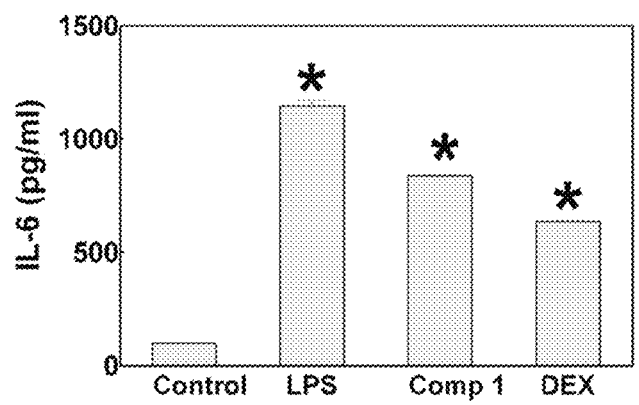

Figure 7

Table 1.

| Accession number[a] | Gene | Name of the gene | p value[b] | Fold change[c] |
|---|---|---|---|---| a) Differentially expressed genes in HCLE cells infected with HSV-1 and treated with compound 1

Overexpressed

| Accession | Gene | Name of the gene | p value | Fold change |
|---|---|---|---|---|
| NM_000584 | IL-8 | *interleukin 8* | 0.000152 | 4.4 |
| NM_000575 | IL-1α | *interleukin 1, alpha* | 0.000157 | 2.9 |
| NM_002089 | CXCL2 | *chemokine (C-X-C motif) ligand 2* | 0.000647 | 2.9 |
| NM_016232 | IL-1RL1 | *interleukin 1 receptor-like 1* | 0.001224 | 5.2 |
| NM_000758 | CSF2 (GM-CSF) | *colony stimulating factor 2 (granulocyte-macrophage)* | 0.001908 | 2.2 | b) Differentially expressed genes in J774A.1 cells activated with LPS and treated with compound 1

Repressed

| Accession | Gene | Name of the gene | p value | Fold change |
|---|---|---|---|---|
| NM_008361 | Il1b | *interleukin 1 beta* | 0.0000379 | 2.58 |
| NM_010090 | Dusp2 | *dual specificity phosphatase 2* | 0.00304884 | 3.86 |

Overexpressed

| Accession | Gene | Name of the gene | p value | Fold change |
|---|---|---|---|---|
| NM_007778 | Csf1 | *colony stimulating factor 1 (macrophage)* | 0.0000844 | 4.42 |
| NM_007498 | Atf3 | *activating transcription factor 3* | 0.000133 | 4.41 |
| NM_021274 | CXCL10 | *chemokine (C-X-C motif) ligand 10* | 0.000353 | 11.41 |
| NM_008352 | Il12b | *interleukin 12b* | 0.000584472 | 4.19 |
| NM_007706 | Socs2 | *suppressor of cytokine signaling 2* | 0.042965613 | 2.29 |
| NM_011414 | Slpi | *secretory leukocyte peptidase inhibitor* | 0.000149 | 1.53 |
| NM_021297 | TLR4 | *toll-like receptor 4* | 0.002540414 | 1.95 |
| NM_010548 | IL-10 | *interleukin 10* | 0.003137306 | 1.27 |
| NM_031168 | IL-6 | *interleukin 6* | 0.004674967 | 1.97 |
| NM_008330 | Ifi47 | *interferon gamma inducible protein 47* | 0.004765124 | 2.49 |
| NM_031252 | Il23a | *interleukin 23, alpha subunit p19* | 0.004775973 | 3.19 |
| NM_019494 | CXCL11 | *chemokine (C-X-C motif) ligand 11* | 0.008359232 | 6.01 |

[a] Accession number in the GeneBank (NCBI). [b] t-Test for paired samples. [c] Relative expression treated/control.

ANTIANGIOGENIC BRASSINOSTEROID COMPOUNDS

FIELD OF THE INVENTION

The present invention relates to the inhibition or prevention of angiogenesis as a means to control or treat an angiogenic dependent condition, a condition characterized by, or dependent upon, blood vessel proliferation.

The present invention describes the use of brassinosteroids of general formula (I)

(I)

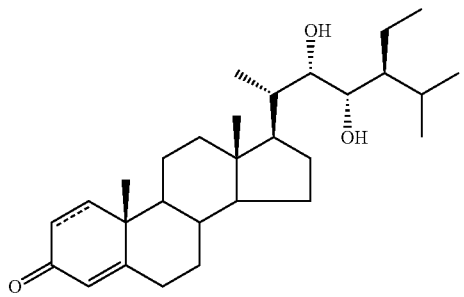

wherein ⌁ can be a single or double bond and the configurations of carbon atoms C22 and C23 respectively linked to the substituents HO are S for both carbon atoms, for inhibiting of angiogenesis in a mammal which has a solid tumor selected from the group consisting of breast carcinoma, lung carcinoma, prostate carcinoma, colon carcinoma, ovarian carcinoma, neuroblastoma, central nervous system tumor, multiform glioblastoma and melanoma.

An embodiment of present invention describes a method of therapeutic treatment for inhibiting of angiogenesis in a mammal which has a solid tumor selected from the group consisting of breast carcinoma, lung carcinoma, prostate carcinoma, colon carcinoma, ovarian carcinoma, neuroblastoma, central nervous system tumor, glioblastoma multiform and melanoma by means of administration of brassinosteroids of general formula (I).

The compounds of general formula (I) are selected from (22S,23S)-22,23-dihydroxystigmast-4-en-3-one (Compound 1) and (22S,23S)-22,23-dihydroxystigmasta-1,4-dien-3-one (Compound 2) which have the following structural formula:

Compound 1

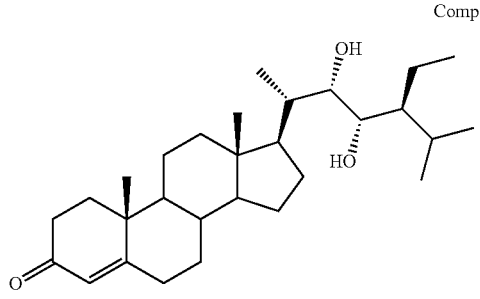

Compound 2

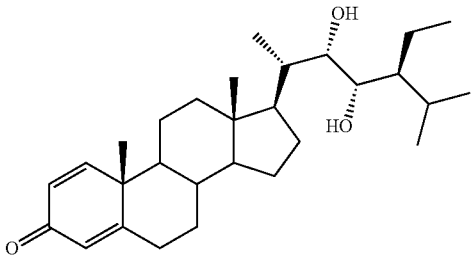

BACKGROUND OF THE INVENTION

Angiogenesis is considered as the development of new blood vessels from existing micro-vessels. This process of generating new blood vessels plays an important role in the development of metastases. Under normal physiological conditions, humans or animals suffer angiogenesis in specific and restricted situations, as example in wound healing, in fetal and embryonal development and in the formation of the corpus luteum, endometrium and placenta. The control of angiogenesis is a highly regulated system involving angiogenic stimulators and inhibitors. The control of angiogenesis has been found to be altered in certain disease states and, in many cases, the pathological damage associated with the disease is related to the uncontrolled angiogenesis.

In tumor angiogenesis, for example, capillary sprouts are formed, their formation being induced by a group of tumor cells. However, compared with blood vessels produced in normal angiogenic microenvironments, tumor micro-vessels are morphologically and functionally unique. Their vascular networks typically show disorganized or aberrant architecture, luminal sizes vary and blood flow can fluctuate chaotically. There are two principal types of tumor angiogenesis in terms of the events which follow implantation of metastatic seedlings on surfaces and in organs. The first or primary angiogenesis is the initial vascularization of the mass of multiplying tumor cells and is regarded as an essential prerequisite for the survival and further growth of a metastatic deposit. The second is a continuing or secondary angiogenesis and is the phenomenon which occurs in waves at the periphery of a growing tumor mass. This second angiogenesis is essential for the accretion of new microcirculatory territories into the service of the expanding and infiltrating tumor.

Angiogenesis is a highly complex process of developing new blood vessels that involves the proliferation and migration of, and tissue infiltration by capillary endothelial cells from pre-existing blood vessels, cell assembly into tubular structures, joining of newly forming tubular assemblies to closed-circuit vascular systems, and maturation of newly formed capillary vessels. The molecular bases of many of these aspects are still not understood.

Angiogenesis is important in normal physiological processes including embryonic development, follicular growth, and wound healing, as well as in pathological conditions such as tumor growth and in non-neoplastic diseases involving abnormal neovascularization, including neovascular glaucoma. Other disease states include but are not limited to, neoplastic diseases, including but not limited to solid tumors, autoimmune diseases and collagen vascular diseases such as, for example, rheumatoid arthritis, and ophthalmological conditions such as diabetic retinopathy, retrolental fibroplasia and neovascular glaucoma. Conditions or diseases to which persistent or uncontrolled angiogenesis contribute have been termed angiogenic dependent or angiogenic associated diseases.

One means of controlling such diseases and pathological conditions comprises restricting the blood supply to those cells involved in mediating or causing the disease or condition. For example, in the case of neoplastic disease, solid tumors develop to a size of about a few millimeters, and further growth is not possible due to absent angiogenesis within the tumor. In the past, strategies to limit the blood supply to tumors have included occluding blood vessels supplying portions of organs in which tumors are present. Such approaches require the site of the tumor to be identified and are generally limited to treatment to a single site, or small number of sites. An additional disadvantage of direct mechanical restriction of a blood supply is that collateral blood vessels develop, often quite rapidly, restoring the blood supply to the tumor. Other approaches have focused on the modulation of factors that are involved in the regulation of angiogenesis. While usually quiescent, vascular endothelial proliferation is highly regulated, even during angiogenesis. Examples of factors that have been implicated as possible regulators of angiogenesis in vivo include, but are not limited to, transforming growth factor beta (TGFβ), acidic and basic fibroblast growth factor (αFGF and (βFGF), platelet derived growth factor (PDGF), and vascular endothelial growth factor (VEGF).

Brassinosteroids have not been used as anti-angiogenic molecule; brassinosteroids are well-known for antiviral activity and as anti-inflammatory and antiviral agents according the following publications:

European Patent Application EP 2178898 refers to brassinosteroids which having anti-inflammatory and antiviral activity which includes the compounds of formula (I) (22S, 23S)-22,23-dihydroxystigmast-4-en-3-one (Compound 1) and (22S,23S)-22,23-dihydroxystigmasta-1,4-dien-3-one (Compound 2).

Publication of Wachsman et al. (Curr. Med. Chem., -Anti-Infective Agents, Antiviral Activity of Natural and Synthetic Brassinosteroids, 2004, Vol. 3, No. 2) refers to the antiviral activity of brassinosteroids which includes the compound (22S,23S)-22,23-dihydroxystigmast-4-en-3-one (Compound 1) included in formula (I) (compound 32b of said publication).

SUMMARY OF THE INVENTION

The present invention refers to a method of treating a solid tumor in a mammal by inhibiting angiogenesis, comprising: administering to the mammal which has a solid tumor selected from the group consisting of breast carcinoma, lung carcinoma, prostate carcinoma, colon carcinoma, ovarian carcinoma, neuroblastoma, central nervous system tumor, multiform glioblastoma and melanoma:

a composition comprising brassinosteroids of general formula (I)

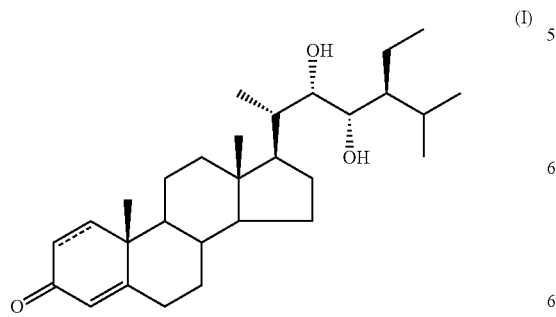

(I)

wherein ⌇ can be a single or double bond and the configurations of carbon atoms C22 and C23 respectively linked to the substituents HO are S for both carbon atoms and a pharmaceutically acceptable additive.

In the method of treating a solid tumor in a mammal by inhibiting angiogenesis, the brassinosteroids of general formula (I) are selected from: (22S,23S)-22,23-dihydroxystigmast-4-en-3-one (Compound 1) and (22S,23S)-22,23-dihydroxystigmasta-1,4-dien-3-one (Compound 2).

Said method of treatment of a solid tumor in a mammal by inhibiting angiogenesis comprises administering to the mammal which has a solid tumor selected from the group consisting of breast carcinoma, lung carcinoma, prostate carcinoma, colon carcinoma, ovarian carcinoma, neuroblastoma, central nervous system tumor, multiform glioblastoma and melanoma:

a composition comprising brassinosteroids of general formula (I), the composition further comprises a second pharmaceutically active agent selected from antiviral, antifungal, antibacterial, antiseptic, anti-inflammatory or immunomodulatory, antineoplastic, anti-angiogenic and analgesic.

In said method of treatment the anti-angiogenic agent is selected from the group consisting of vincristine, vinblastine, vinorelbine, vindesine, paclitaxel, docetaxel, 5 FU, cisplatin, carboplatin, irinotecan, topotecan and cyclophosphamide.

The present invention further refers to a use of a brassinosteroids of general formula (I)

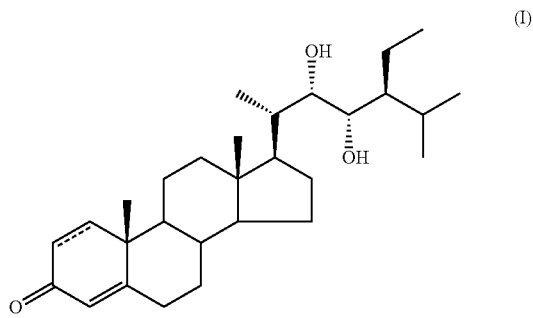

(I)

wherein ⌇ can be a single or double bond and the configurations of carbon atoms C22 and C23 respectively linked to the substituents HO are S for both carbon atoms, for the manufacturing a composition for treating solid tumor selected from the group consisting of breast carcinoma, lung carcinoma, prostate carcinoma, colon carcinoma, ovarian carcinoma, neuroblastoma, central nervous system tumor, multiform glioblastoma and melanoma in a mammal by inhibiting angiogenesis.

In said use of the brassinosteroids of general formula (I) for the manufacturing a composition for treating solid tumor, said brassinosteroids of general formula (I) are selected from: (22S,23S)-22,23-dihydroxystigmast-4-en-3-one (compound 1) and (22S,23S)-22,23-dihydroxystigmasta-1,4-dien-3-one (compound 2). In said use of the brassinosteroids of general formula (I) for the manufacturing a composition for treating solid tumor, the composition further comprises a second pharmaceutically active agent selected from antiviral, antifungal, antibacterial, antiseptic, anti-inflammatory or immunomodulatory, antineoplastic, anti-angiogenic and analgesic.

In said use the anti-angiogenic agent is selected from the group consisting of vincristine, vinblastine, vinorelbine, vindesine, paclitaxel, docetaxel, 5 FU, cisplatin, carboplatin, irinotecan, topotecan and cyclophosphamide.

DESCRIPTION OF THE DRAWINGS

FIG. 3. A-F) NF-κB nuclear translocation in macrophages treated with Compound 1.

J774A.1 cells were stimulated with LPS for 8 h, and treated or not with 40 μM of Compound 1 or DEX. The localization of p65 was detected by IFI staining in methanol fixed cells. Magnification:400×. (A) Control cells; (B) non-stimulated cells treated with Compound 1; (C) non-stimulated cells treated with DEX; (D) LPS-stimulated cells; (E) LPS-stimulated cells treated with Compound 1; (F) LPS-stimulated cells treated with DEX. G) Secretion of IL-6 in macrophages treated with Compound 1. J774A.1 cells were stimulated with LPS for 8 h, and then were treated or not with 40 μM of Compound 1 or DEX. IL-6 was determined by ELISA in the supernatants. *p<0.005, with respect to untreated stimulated cells and to untreated non-stimulated cells.

Figure 4:
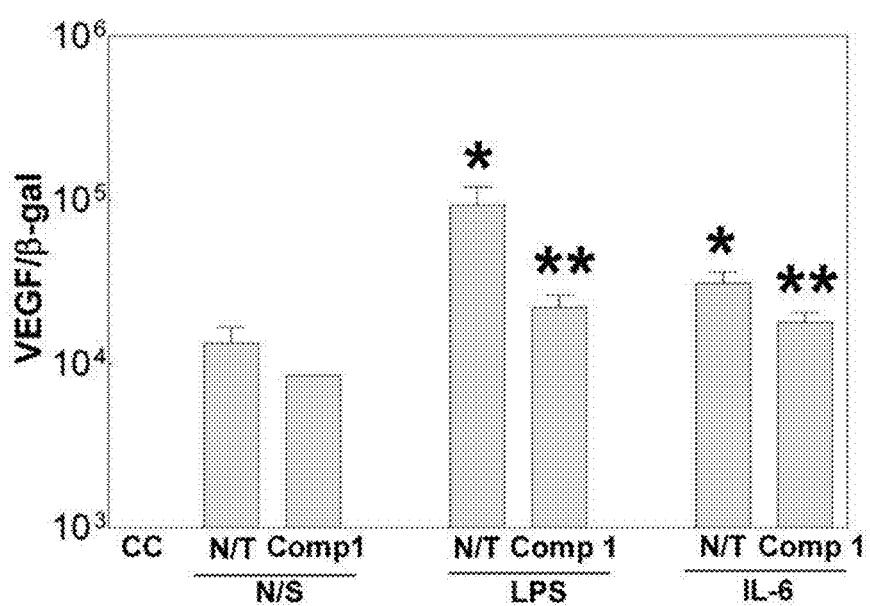

FIG. 4. Effect of Compound 1 on VEGF expression in J774A.1 cells stimulated with LPS and IL-6. Cells grown in 6-well microplates were transfected with pVEGF-LUC y pb-gal, as a control and, 24 h post-transfection they were stimulated with 100 ng/ml LPS or 1 ng/ml IL-6. After 8 h of induction with LPS and 16 h with IL-6, cells were harvested and luciferase expression was measured as a reporter of VEGF promoter activity. Luciferase values were normalized to b-gal activity. CC: non transfected cells; N/S: non-stimulated transfected cells; N/T: no-treatment. (* and **, significantly different with respect to the control. p values are reported in the text).

Figure 5:
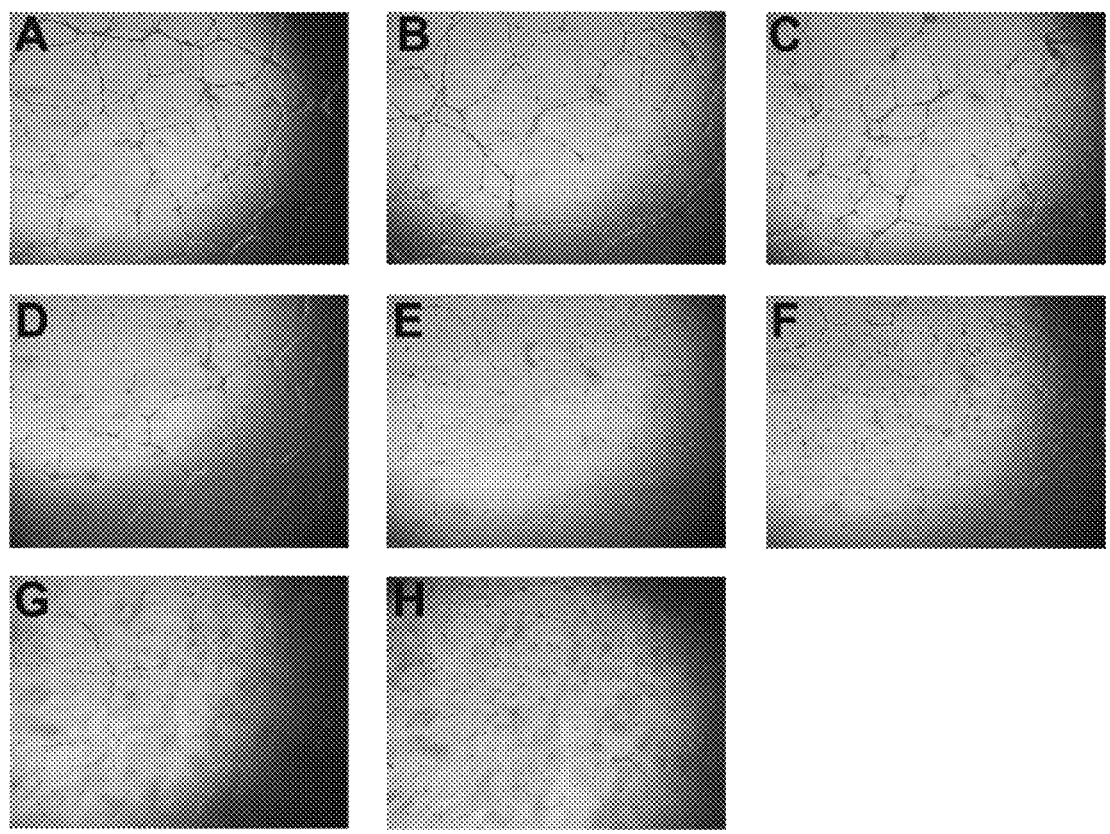

FIG. 5. Effect of Compound 1 on capillary tube formation on a Matrigel. HUVEC cells were seeded on polymerized Matrigel (5 to 8×10⁴ cells/well) in the absence and presence of different concentrations of Compound 1. The plate was incubated at 37° C., and tube formation was observed under an optic inverted microscope. Digital pictures were taken at 24 h of incubation. Magnification: 25×.

Figure 6:
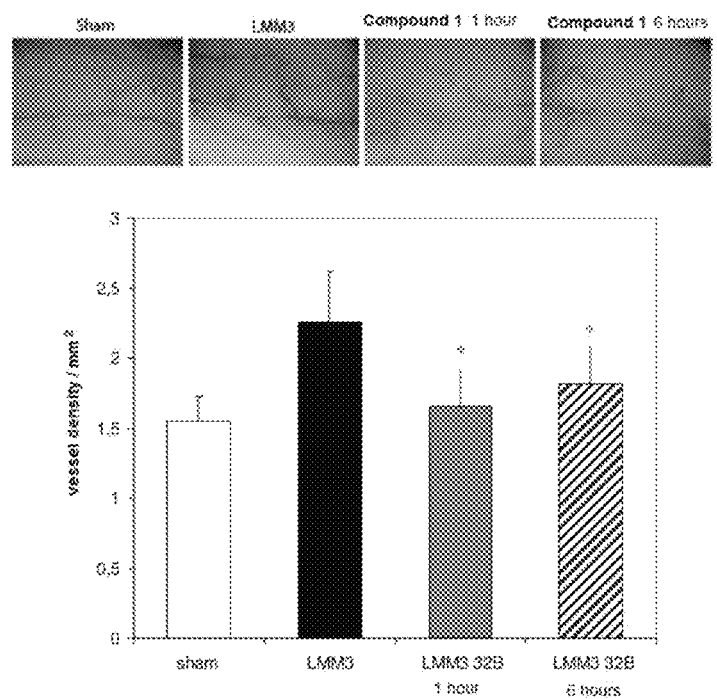

FIG. 6. Antiangiogenic effect of Compound 1 on the in-vivo neovascular response induced by LMM3 cells in BALB/c mice. 2×105 cell/0.1 mL were inoculated in the side of each BALB/c mice. Five days after the inoculation the animals were sacrificed and photographs of the inoculation site were taken. The upper panel shows representative pictures of each experimental group. In the graph, the vessel density (vessels/mm2) is shown as quantified for each group+/−ES*p<<0.001 vs LMM3.

FIG. 7. Differential gene expression in HCLE cells infected with HSV-1 and J774A.1 stimulated with LPS and treated with Compound 1. HCLE cells infected with HSV-1 (m.o.i.=1) and J774A.1 stimulated with 100 ng/ml LPS, in both cases treated with 40 μM of Compound 1 for 6 h. Total RNA extraction with Trizol and analysis of gene expression profiles of human and mice cells through the two-color Microarray Agilent.

DETAILED DESCRIPTION OF THE INVENTION

Herpes simplex virus type 1 (HSV-1) induces a chronic ocular inflammatory syndrome called herpetic stromal keratitis (HSK) that can lead to blindness. This immunopathology develops as a consequence of the arrival of inflammatory cells to the cornea in response to infection through the appearance of new blood vessels. While inflammatory cells are responsible for the elimination of HSV-1 from the eye, they cause an uncontrolled inflammatory response that culminates in the development of the HSK.

The compound (22S,23S)-22,23-dihydroxystigmast-4-en-3-one (Compound 1) has the following structural formula:

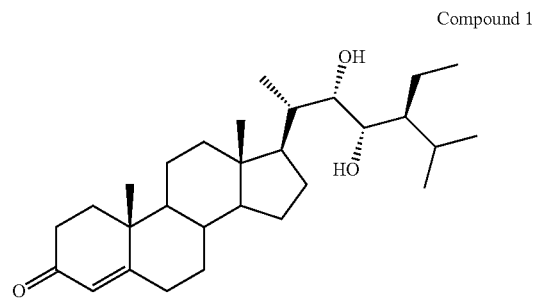 [SMILES: CC[C@@H](C(C)C)[C@H](O)[C@@H](O)[C@@H](C)[C@H]1CCC2C3CCC4=CC(=O)CC[C@]4(C)C3CC[C@@]21C]

Compound 1

The compound (22S,23S)-22,23-dihydroxystigmast-4-en-3-one (Compound 1) exerts an antiviral activity in epithelial cells derived from ocular tissue (HCLE and NHC) and reduces the incidence of HSK in the murine model of HSV-1 ocular infection. To study a possible immunomodulatory action of the compound which would explain the improvement of murine HSK, we investigated the effect of Compound 1 in the modulation of the epithelial and immune cells to various stimuli. Compound 1 proved to elicit the release of pro-inflammatory cytokines like TNF-α, IL-6 and IL-8 in HSV-1-infected epithelial cells from ocular origin and, on the other hand, significantly reduced TNF-α and IL-6 production in LPS-activated macrophages.

DNA microarray tests performed on samples of HCLE cells infected with HSV-1 and J774A.1 cells stimulated with LPS, both treated with the stigmastane, revealed various over-expressed and repressed genes associated with innate immune responses and inflammatory processes. We corroborated the inhibitory effect of Compound 1 on activated inflammatory cells and an immunostimulatory activity in infected epithelial cells.

The pro-inflammatory effect of Compound 1 in infected cells would favor the activation of the innate immune response responsible for removing the virus from them. Besides, it would inhibit pro-inflammatory factors and stimulate anti-inflammatory mediators in macrophages activated with LPS, suggesting an immunosuppressive action on inflammatory cells. The balance between pro and anti-inflammatory effects of the stigmastane could explain the improvement of HSK in infected mice. In addition, the improvement of the signs of murine neovascularization after the treatment with Compound 1 would also be ascribed to the inhibition of capillary-like structures observed in vitro.

Method of obtaining Compound 1: (22S,23S)-22,23-dihydroxystigmast-4-en-3-one

In a balloon provided with a refrigerant, in an inert atmosphere, 15 grams of stigmasterol in 750 ml of toluene anhydride are dissolved. 25 ml of N-methyl-4-piperidone are added; the mixture is stirred and boiled until 50 ml of solvent are distilled.

The mixture is cooled to 60° C., and 7 grams of aluminum isopropoxide are added. The solution is refluxed during 3 hours, and taken to ambient temperature and successively washed with 200 ml of 5% aqueous hydrochloric acid, 100 ml of aqueous sodium bicarbonate and finally water. Toluene is evaporated at reduced pressure and the resulting solid is recrystallized from methanol. 12.3 grams of (22E)-stigmast-4-en-3-one are obtained, melting point 127-128° C.

The product obtained is dissolved in a mixture consisting of 500 ml tetrahydrofuran and 100 ml water, and 1.5 grams of sodium bicarbonate, 10 mL tert-butanol, 2.8 grams of methanesulphonamide and 150 mg osmium tetroxide are added.

The resulting solution is heated to 50° C. during 24 hours and taken to ambient temperature. 12 grams of sodium bisulphate dissolved in 100 ml water are added. The volume of solvent is reduced to reduced pressure to about 300 mL. The mixture obtained is extracted 3 times with 100 mL of ethyl acetate. The organic extract is dried with sodium sulphate anhydrous and evaporated to dryness at reduced pressure.

The crude product is purified by silica column chromatography (eluting solvent: hexane/ethyl acetate 1:1). 8.9 grams of (22S,23S)-22,23-dihydroxystigmast-4-en-3-one are obtained.

$^1$H-RMN (CDCl$_3$, 200 MHz): 5.72 (1H, s, H-4); 3.61 (2H, m, H-22 and H-23).

$^{13}$C-RMN (CDCl$_3$, 50 MHz): 198.4 (C-3); 170.4 (C-5); 123.9 (C-4); 72.3 (C-22); 70.7 (C-23). IR: 3300 and 1680 cm$^{-1}$.

Assays:

1.—Introduction

Herpetic stromal keratitis (HSK) results from an infection with Herpes simplex virus type 1 (HSV-1) in the cornea. The initiation of disease requires viral replication in the epithelial cells, and its progression may lead to blindness. In fact, visual morbidity results from recurrent keratitis, which provokes corneal scarring, thinning and neovascularization due to the immune response to virus. The ability of HSV-1 to cause corneal stromal disease is correlated with its facility to induce corneal vascularization. The invasion of the cornea by PMN through the new vessels helps in clearing the virus but, at the same time, lends entry to various cytokines and angiogenic factors secreted by the inflammatory cells. The pathogenesis of corneal scarring and vascularization is uncertain, but appears to be a complex interaction of various cytokines, chemokines and growth factors, such as interleukin (IL)-1α, IL-1β, IL-8, IL-6, IL-12, IL-17, interferon (IFN)-α, tumor necrosis factor (TNF)-α, macrophage inflammatory protein (MIP)-2, monocyte chemotactic proteins (MCP)-1, IL-12 and MIP1-α, vascular endothelial growth factor (VEGF) and matrix metalloproteinase (MMP)-9, either brought in by the inflammatory cells or locally released by infected and neighboring cells in the early response to HSV-1 infection.

Previously, we have reported that polyfunctionalized stigmastane derivatives have antiviral activity against several pathogen viruses in vitro and, particularly, prevent HSV-1 multiplication and viral spreading in both human corneal and conjunctival cell lines, with no cytotoxicity. One of these compounds, (22S,23S)-3β-bromo-5α,22,23-trihydroxystigmastan-6-one, designated also as Compound 6b in the publication of Wachsman et al. (Curr. Med. Chem., -Anti-Infective Agents, Antiviral Activity of Natural and Synthetic Brassinosteroids, 2004, Vol. 3, No. 2), significantly decreases the incidence of HSK in the murine model of HSV-1 corneal infection, probably due to an immunomodulatory effect, since it does not exert an anti-HSV-1 activity in vivo.

Compound 6b has the following structural formula:

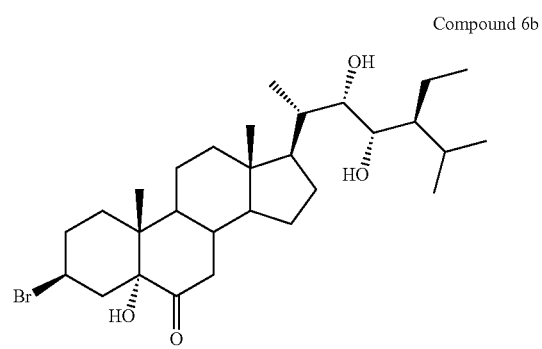 [SMILES: CC[C@@H](C(C)C)[C@H](O)[C@@H](O)[C@@H](C)[C@H]1CCC2C3CC(=O)[C@@]4(O)C[C@@H](Br)CC[C@]4(C)C3CC[C@@]21C]

Compound 6b

Furthermore, this stigmastane derivative hinders the production of TNF-α in LPS-stimulated macrophages in vitro and modulates the secretion of IL-6 and TNF-α in human epithelial cells derived from ocular tissues. In order to improve the immunomodulatory activity of these kind of molecules, we designed stigmastane analogs, keeping the (22S,23S)-22,23-dihydroxylated side chain of the steroidal structure and providing A and B rings, with structural features similar to those of the commercial anti-inflammatory drug Dexamethasone (DEX). We found that one of these synthesized stigmastane analogues, (22S,23S)-22,23-dihydroxystigmast-4-en-3-one, designated as Compound 1, also prevents HSV-1 multiplication and viral spreading in human conjunctival and corneal cells, with no cytotoxicity, with selectivity indices (SI) of 13.2 and 9.3, respectively.

We observed that this stigmastane significantly decreases the incidence and severity of HSK in the murine model of HSV-1 corneal infection, not only in the presence of replicative virus like stigmastane 6b (or Compound 6b) does, but also when viral replication had already triggered the immune response. Thus, Compound 1 turned out to be interesting as a future drug for the treatment of HSK since its healing potential would also be due to an immunomodulatory effect. Conversely, Compound 1 would not behave as a conventional steroidal anti-inflammatory drug, like DEX, since it significantly restrained the signs of keratitis when administered during the first 3 days after HSV-1 infection, while DEX exacerbated ocular damage.

In an attempt to explain the improvement of murine HSK previously reported, we evaluated the role of Compound 1 both, as a modulator of the immune response to viral infection and to a non viral stimulus, and as an anti-angiogenic drug in vitro.

2. Materials and Methods 2.1. Cells, Viruses and Treatment Solutions

Human IOBA-NHC cell line was grown in Dulbecco's modified medium and nutrient mixture F-12 (DMEM/F12, 1:1), supplemented with 10% inactivated FBS (DMEM/F12, 10%), and maintained in DMEM/F12 supplemented with 2% inactivated FBS (DMEM/F12, 2%).

Human corneal-limbal epithelial cells (HCLE) were kindly provided by Dr. Ilene K. Gipson and Dr. Pablo Argüeso (The Schepens Eye Research Institute, Harvard Medical School, Boston, USA) and grown in GIBCO Keratinocyte Serum Free Medium, supplemented with 25 μg/ml bovine pituitary extract (BPE), 0.2 ng/ml epidermal growth factor (EGF) and 0.4 mM CaCl2, and maintained in low calcium DMEM/F12.

Murine macrophage cell line J774A.1 was kindly provided by Dr. Osvaldo Zabal (INTA, Castelar, Buenos Aires) and grown in RPMI 1640 medium supplemented with 10% inactivated FBS (RPMI 10%) and maintained in RPMI supplemented with 2% inactivated FBS (RPMI 2%).

Human umbilical vein endothelial cells (HUVECs) were obtained from Invitrogen Argentina S.A., Buenos Aires, Argentina, and were propagated and maintained in Medium 200 supplemented with LSGS.

The HSV-1 KOS strain was propagated at low multiplicity and used for in vitro experiments.

Compound 1 was dissolved in dimethylsulfoxide (DMSO) and diluted with culture medium. The maximum concentration of DMSO tested was 1% and exhibited no cytotoxicity under experimental conditions.

Dexamethasone 0.4% (DEX) was purchased from Sidus, *Argentina*.

2.2. Cytotoxicity Assay

Cell viability was determined as previously reported. The absorbance of each well was measured on a Eurogenetics MPR-A 4i microplate reader using a test wavelength of 570 nm and a reference wavelength of 630 nm. Results were expressed as a percentage of absorbance of treated cells with respect to untreated ones. The CC50 was defined as the concentration of compound that caused 50% reduction in cell viability.

2.3. Indirect Immunofluorescence

IOBA-NHC and HCLE cells monolayers grown on coverslips in 24-well plates were infected with 0.2 ml of HSV-1 KOS (m.o.i.=1) and incubated 1 h at 37° C. Then, the inoculums were removed and cells were coated with a DMEM/F12 without SFB, for 24 h at 37° C.

J774A.1 cells were grown on coverslips in 24-well plates and stimulated with 100 ng/ml LPS (Sigma) in RPMI without SFB, for 8 h at 37° C.

After incubation, cells were fixed in methanol at −20° C. for 10 min, and processed for indirect immunofluorescence (IFI) with antibodies directed against the glycoprotein D (gD) of HSV-1 and/or the p65 subunit of NF-κB. After three washes with PBS, the coverslips were inverted on a drop of a 1/100 dilution of the first antibody, mouse monoclonal anti-gD and/or rabbit polyclonal anti p65 (Santa Cruz Biotechnology) and incubated for 30 min at 37° C., and then subjected to three additional washes with PBS. Then, the coverslips were incubated with a dilution 1/50 of the second antibodies, polyclonal goat anti-mouse IgG FluoroLink™ Cy™3 and/or anti-goat polyclonal IgG rabbit conjugated to FITC (Sigma Aldrich) for 30 min at 37° C.

Finally, the coverslips were rinsed first with PBS and then with distilled water, mounted with buffered glycerin and observed under a Zeiss microscope with epifluorescence optics or a confocal microscope Olympus FB300.

2.4. Quantitative Analysis of Fluorescence

The images obtained with a 40× magnification were imported into NIH Image J 1.34s program (designed by Wayne Rasband, NIMH, Bethesda). Immunofluorescence images were converted to a grayscale of 8 bit from 0 (black) to 255 (white). We analyzed the total and nuclear fluorescence of the individual cells and a mean fluorescence density was obtained for each. To compare the distribution of fluorescence within the cell, the results were analyzed in a spreadsheet (Excel®). The total fluorescence intensity or nuclear density was calculated as the total or nuclear average per total or nuclear area, respectively. Then, we calculated the percentage of nuclear intensity or the percentage of nuclear intensity with respect to the total intensity for each cell. Non-stimulated cells were processed to establish a baseline of nuclear fluorescence (cut-off value).

2.5. Cytokine Determination

IOBA-NHC and HCLE cells grown in 24-well plates were infected with HSV-1 (m.o.i.=1), in duplicate. After 24 h of incubation at 37° C., supernatants were harvested, centrifuged at 1000 rpm for 10 min, and cytokines were quantified by ELISA. Human TNF-α, IL-6 and IL-8 were quantified by commercial ELISA sets (BD OptEIA™, Becton Dickinson, USA), according to manufacturer instructions.

J774A.1 cells grown in 24-well plates were incubated at 37° C. with 100 ng/ml of LPS, in duplicate. After 8 h, supernatants were harvested and murine IL-6 was quantified by commercial ELISA sets (BD OptEIA™, Becton Dickinson, USA) according to manufacturer instructions.

2.6. Microarray Procedures

HSV-1 infected cells and LPS stimulated cells were transcriptionally analyzed by using the whole human genome microarray and whole mouse genome microarray (Agilent Technologies, Santa Clara, Calif.), corresponding to 41,000 human or mice genes and transcripts.

2.6.1. Determination of Gene Expression Profiles

RNA was extracted with chloroform/isopropanol and purified from Trizol. Processed samples were quantified in a spectrophotometer (NanoDrop), exhibiting a high content of total RNA (1800 and 3100 ng/ml), and a good quality without degradation, according to the graphs obtained from the Bio-analyzer 2100 (Agilent Technologies).

cDNA synthesis, amplification and labeling of cRNA was performed, following the protocol of two colors of Agilent. Cyanine: 3-CTP and 5-CTP labeled cRNA was prepared from purified RNA (Two-Color Microarray-Based Gene Expression Analysis—Quick Amp Labeling, Agilent). Labeled cRNA was purified, quantified and the efficiency of labeling determined.

After that, we proceeded with the hybridization, washing, assembling of the chips and scanning. The scanner software (Feature extraction) performed the scan quality control. The fluorescence intensity data obtained for each chip were analyzed using GeneSpring XG11 and Multi Experiment Viewer (MeV) programs.

Labeled samples were placed in human and mouse hybridizing chips for HCLE and J774A.1 cells, respectively, during 17 h at 60° C. Successive washings were done with different washing, stabilization and drying solutions, and samples were scanned in the Agilent scanner G2565BA.

2.6.2. Image Analysis

We used the commercial software Agilent Feature Extraction for quality control of the scan. The software converts the scanned images produced in quantitative data for further analysis. It calculates the errors associated with hybridization, washing and scanning and detects outliers. On the one hand, it performs an analysis of the image to locate the grid on the chip and in it, the spots for each gene, and on the other hand, it makes an analysis of data, to define and measure information (fluorescence intensity) of each spot, for the analysis of gene expression.

2.6.3. Data Analysis

We identified differentially expressed genes with statistical significance. We used two programs, the XG11 and Gene-Spring and the Multi Experiment Viewer (MeV).

2.7. VEGF Expression

The expression vectors pVEGF-LUC (encoding firefly luciferase) and pβ-gal were kindly donated by members of the research group of Dr. Arzt (FCEyN, UBA, Argentina).

J774A.1 cells grown to confluence in 6-well micro-plates were transfected with 0.5 g of pVEGF-LUC and pβ-gal plasmids diluted in the Opti MEM medium, without serum and antibiotics, and in the presence of lipofectamine (DNA lipofectamine TM 2000) as a reagent for transfection, according to the manufacturer's instructions. After 4 to 6 h of incubation at 37° C. in 5% $CO_2$ atmosphere, the medium was discarded and replaced by fresh Opti MEM with 10% FBS, without antibiotics, and incubated at 37° C. in atmosphere 5% $CO_2$ for 24 h.

The medium was discarded and cells were stimulated with 100 ng/ml LPS and 1 ng/ml of IL-6 in Opti MEM medium with 10% FBS. After 8 h and 16 h stimulation, the medium was discarded and the cells were lifted by scrapping in 0.1 ml per well of 1× lysis buffer. The samples were stored at −70° C. until processing.

In order to measure luciferase activity, 20 μl of each sample were mixed with 80 μl of substrate for firefly luciferase and measured in a luminometer. In the same samples, β-gal activity was measured in 96-well microplates. To do this, 20 μl of each sample were mixed with 80 μl of substrate for β-galactosidase and incubated at 37° C. until color developed. The absorbances of these mixtures were read in an ELISA reader at 450 nm.

We determined the expression of luciferase as a reporter of VEGF promoter activity values obtained by normalizing the against β-gal activity for each sample.

2.8. Capillary Tube Formation on a Matrigel

The formation of capillary tube like structures by HUVEC cells was analyzed on 24-well cell culture plates coated with an extracellular membrane matrix (Matrigel; BD Biosciences).

Matrigel was thawed at 4° C. Using precooled plates and tips, 100 μl/well of Matrigel was distributed and allowed to gelify at 37° C. for at least 30 min. Cells were seeded on the polymerized Matrigel (5 to $8 \times 10^4$ cells/well). The plate was incubated at 37° C., and tube formation was observed under a optic inverted microscope. Digital pictures were taken at different times with a camera. Tubular structures were quantified by manual counting of low power fields (25×) and inhibition percentage was expressed using untreated wells as 100%.

2.9. Cell Invasion Assay

HUVECs' invasion was evaluated using 24-well transwell cell culture chambers with 8 μm pore polycarbonate filter inserts. Cultured HUVECs were trypsinized and suspended in Medium 200 supplemented with LSGS at a concentration of $8 \times 10^5$ cells/ml. A total of $4 \times 10^4$ of cell suspension was applied to insert filters. We used 100 ng/ml of IL-6 to stimulate cell migration through the inserts. For that, we dispensed 600 μl of medium alone or with the stimulus in the lower chamber, which was then incubated for 24 h at 37° C. to allow cell migration. The insert was removed and migrated cells on the wells were fixed and stained with crystal violet. The wells were examined under a microscope. Migration was quantified by measuring the total stained cells in every well.

3.0. Statistical Analysis

Student's t-test was used for statistical analysis of all data.

Results

1. Immunomodulating Activity of Compound 1 in HSV-1 Infected Epithelial Cells 1.1. NF-κB Activation is not Affected by Compound 1 after HSV-1 Infection The improvement of mice with HSK when treated with Compound 1 seems not to be related either to an early viral clearance or to an anti-inflammatory effect of the compound comparable to that observed after treatment with DEX at the onset of disease. Hence, we speculated that the effect exerted by the stigmastane would be involved in the innate immune response displayed during the first stages of HSV-1 infection. Since HSV-1 is able to activate NF-κB, we investigated the effect of Compound 1 on NF-κB p65 subunit intracellular localization. For that purpose, IOBA-NHC and HCLE cells were infected with HSV-1 (m.o.i.=1) and treated or not with Compound 1 (40 μM). A double IFI staining was performed by adding anti-p65 and anti-HSV-1 gD antibodies so as to visualize gD as a marker of viral infection.

Figure 1:
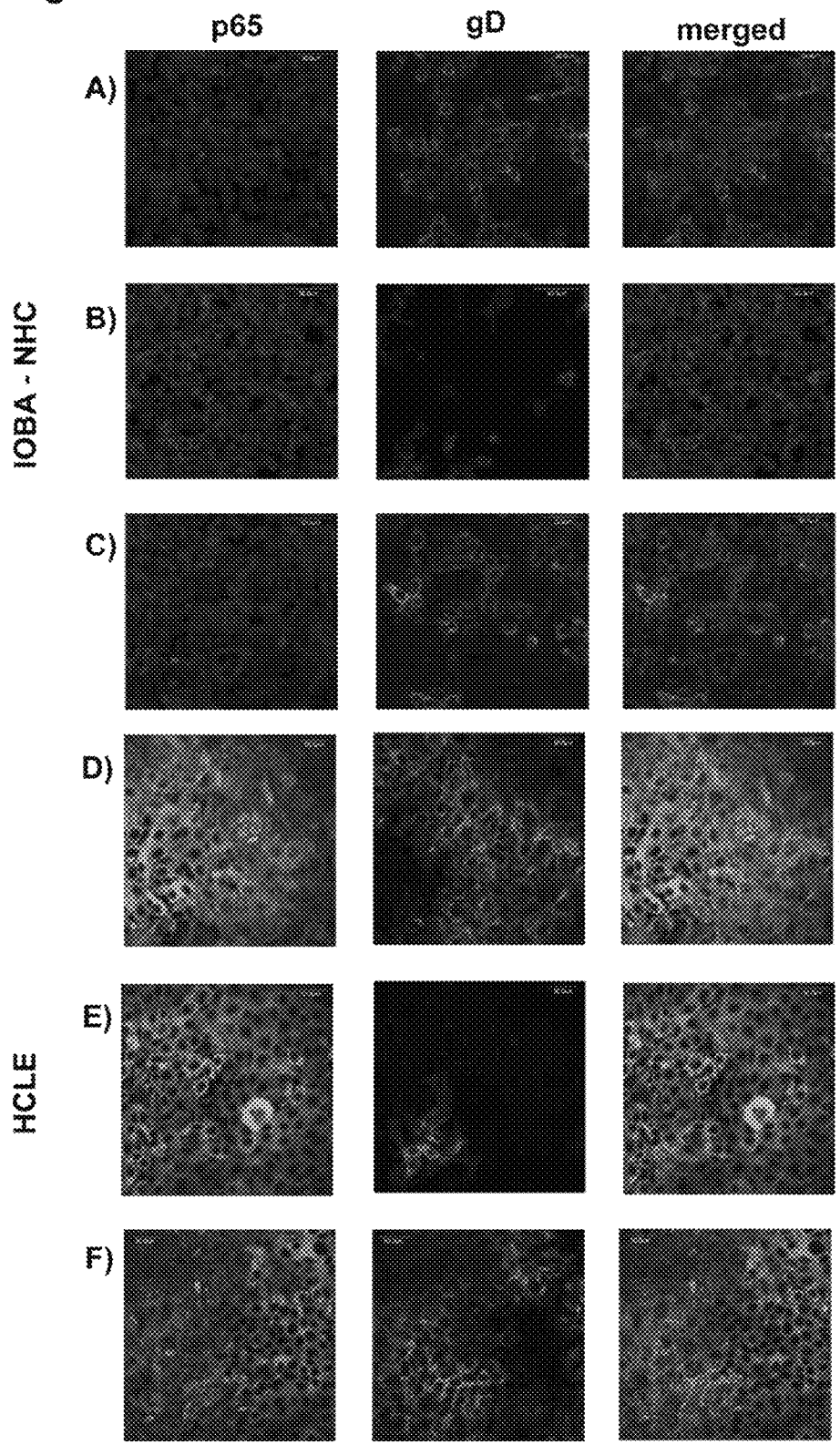
FIG. 1. Effect of Compound 1 on NF-κB nuclear translocation induced by HSV-1. IOBA-NHC and HCLE cells were infected with HSV-1 (m.o.i.=1) in the absence or presence of 40 μM of Compound 1. Double IFI staining was performed by adding anti-p65 and anti-HSV-1 gD antibodies to methanol fixed cells. NF-κB translocation and gD expression were analyzed by confocal microscopy. (A and D) infected cells; (B and E) infected cells treated with 40 μM of Compound 1; (C and F) infected cells treated with 40 μM of DEX. Magnification: NHC, 400× and HCLE, 600×.

We found that the majority of infected IOBA-NHC and HCLE cells exhibited p65 fluorescence in the nuclei (85.9% and 72.5%, respectively) (FIGS. 1A and D). Most of them clustered in characteristic HSV-1 foci showing nuclear p65 fluorescence associated with gD staining. When Compound 1 was added, the percentage of cells exhibiting NF-κB translocation to the nucleus dropped to 22.2±1.2% in IOBA-NHC (FIG. 1B) and 5.7% in HCLE cells (FIG. 1E). In the presence of the compound, the number of cells with nuclear p65 fluorescence diminished considerably, coincidentally with the limited appearance of fewer and scattered foci expressing gD. Compound 1 inhibits NF-κB translocation, although this effect could be ascribed to its anti-HSV-1 effect. On the other hand, treatment with DEX did not prevent NF-κB nuclear translocation in none of HSV-1 infected cells (FIGS. 1C and F).

1.2. Modulation of Cytokine Production by Compound 1 in Infected Epithelial Cells Corneal cells are the first line of defense against HSV-1 and, together with conjunctival cells, they release pro-inflammatory cytokines such as TNF-α, IL-8 and IL-6, associated with the elimination of the infectious agent. Furthermore, NF-κB is closely related to the production of these and other pro-inflammatory cytokines after induction with various stimuli.

Therefore, to further analyze the immunomodulatory activity of the stigmastane, we studied its effect on the production of TNF-α, IL-6 and IL-8 in both cellular types.

IOBA-NHC and HCLE cells infected with HSV-1 (m.o.i.=1) were treated or not with 40 μM of Compound 1 and DEX. After 24 h, cell supernatants were harvested and TNF-α, IL-6 and IL-8 were quantified by ELISA.

Compound 1 did not induce TNF-α release by itself in uninfected treated cells. Besides, HCLE cells failed to produce TNF-α regardless supernatants belonged to HSV-1-infected or HSV-1-infected and treated cells, whereas IOBA-NHC cells were weak TNF-α producers. Uninfected cells yielded 40.9 pg/ml of the cytokine, whereas HSV-1 infection raised TNF-α yield to 77.1 μg/ml (p<0.01) (FIG. 2A). DEX abrogated TNF-α production in HSV-1 infected IOBA-NHC cells completely, whereas Compound 1 did not affect TNF-α production (FIG. 2A).

The pattern of HSV-1-induced IL-6 expression varied depending on the cellular type.

IL-6 production was ten-fold higher in IOBA-NHC infected cells than that detected in HCLE cells (FIGS. 2B and C). Noteworthy, Compound 1 did not elicit any change in IL-6 release from neither infected cell types with respect to infected control cells, whereas IL-6 level was considerably reduced after treatment with DEX. Compound 1 did not induce IL-6 release by itself in uninfected treated cells.

IOBA-NHC and HCLE cells displayed high basal levels of IL-8 secretion-522.5±23 μg/ml and 133.8±0.6 pg/ml, respectively—which were considerably increased after treatment with Compound 1 alone (p<0.01) (FIGS. 2D and E; data not shown). HSV-1 infection provoked a reduction in IL-8 secretion in IOBA-NHC cells to 252±7.8 pg/ml (p<0.001), infected HCLE cells showed a low but significant increase in IL-8 secretion, from 133.8±0.6 pg/ml to 142.9±0.5 pg/ml (p<0.01). Treatment of infected cells with Compound 1 induced a significant augment of IL-8 with respect to untreated infected IOBA-NHC and HCLE cells (471.8±30 pg/ml, p<0.001 and 163.6±0.4 pg/ml, p<0.00001, respectively). Unlike Compound 1, DEX slightly, but significantly, reduced IL-8 secretion both in uninfected and infected conjunctival and corneal cells (p<0.001) (FIGS. 2D and E).

In summary, Compound 1 proved to elicit the release of pro-inflammatory cytokines in HSV-1 infected epithelial cells from ocular origin, while DEX produced an effect as an anti-inflammatory drug, revealing a different behavior of both structurally related compounds.

2. Immunomodulating Activity of Compound 1 in Activated J774A.1 Cells 2.1. Compound 1 Abrogates IL-6 Secretion from Activated J774A.1 Cells Macrophages are involved in the inflammatory response in the eye during the development of HSK. These cells are not present in the healthy cornea, but have been detected in this region of the eye after experimental infection of mice with HSV-1. The contribution of macrophages in the amplification of the inflammatory response occurs through the secretion of pro-inflammatory molecules such as TNF-α and IL-6.

We have already shown that Compound 1 is effective to diminish TNF-α secretion in activated macrophages even more than DEX, given that the inhibitory concentration 50% (IC50) value for Compound 1 was 7 µM, and 48 µM for DEX (manuscript in preparation). This result prompted us to evaluate the effect of the compound on the secretion of IL-6.

Non-stimulated macrophages exhibited a basal production of 100 ng/ml IL-6, while 100 ng/ml of LPS raised the levels to a concentration of 1.146,8±25.9 pg/ml of this cytokine (FIG. 3G).

Compound 1 exerted a strong inhibition of IL-6 yield, since its level was significantly lowered to 838±4.2 pg/ml (p<0.005) in activated macrophages with respect to untreated control cells (FIG. 3G). In the case of treatment with DEX, the production of IL-6 was also restrained (637.1±3.8 pg/ml; p<0.005) (FIG. 3G).

2.2. NF-κB Activation is not Induced by Compound 1 in Stimulated J774A.1 Cells

To verify whether the reduction on cytokine secretion exerted by Compound 1 was associated with a blockage in NF-κB activation, we evaluated the effect of the compound on p65 subunit nuclear translocation in macrophages.

After 8 h of stimulation with LPS, p65 was detected in the nucleus of the majority of the cells, whereas non-stimulated cells showed a cytoplasmic localization (FIGS. 3D and 3A). p65 was detected in the nuclei of stimulated-treated cells, indicating that Compound 1 did not prevent NF-κB translocation (FIG. 3E). The semi quantitative analysis of the images showed a basal nuclear fluorescence of 33.6±8.7% in non-stimulated macrophages. A percentage of 79.4±1.2 of LPS stimulated cells exhibited a nuclear fluorescence value above the basal, which meant positive for NF-κB translocation to the nucleus. NF-κB activation was evidenced in 87.9±0.2% of macrophages induced with LPS and treated with Compound 1.

Unexpectedly, treatment with DEX did not succeed in preventing NF-κB translocation, since 100% of the cells exhibited p65 fluorescence in the nucleus, unlike the results described by Lavagno et al. (2004) (FIG. 3F).

Nevertheless, it is remarkable that p65 localized in the nuclei even when LPS stimulated cells treated either with Compound 1 or DEX, showed a reduction in the secretion of both, IL-6 and TNF-α mediators (FIG. 3G).

3. Gene Expression in Epithelial and Inflammatory Cells is Affected by Compound 1

Since Compound 1 proved to behave as an immunomodulator in vitro regardless the stimuli used (viral or non-viral), we investigated if these findings correlated to an altered cell gene expression. For this purpose, epithelial infected and inflammatory cells were processed to obtain RNA samples. HCLE cells infected with HSV-1 (m.o.i.=1) and J774A.1 cells stimulated with LPS (100 ng/ml) were treated or not with 40 µM of Compound 1. To extract total RNA, cells were harvested with Trizol at 6 h p.i. and at 6 h post-LPS induction. Eight replicates were obtained from HSV-1 infected and LPS-stimulated cells (four 'control' each) and other eight, from infected and LPS-stimulated cells treated with Compound 1 (four 'treated' each).

According to the Gene Onthology analysis performed by the Gene Spring program, we conclude that Compound 1 elicited the activation or inhibition of inflammatory processes or processes related to the innate immune response, evidenced by differentially expressed genes from epithelial cells infected with HSV-1 and inflammatory cells stimulated with LPS. Table illustrates those genes we found more relevant for analysis.

Our results showed that Compound 1 induced overexpression of IL-1α, IL-8 and CXCL-2 in HCLE cells infected with HSV-1, compared to infected and untreated controls (Table 1).

HSV-1 corneal infection induces IL-1α secretion. IL-1α, in turn, induces the production of CXCL-2 in corneal resident cells. Other chemokines such as IL-8 (CXCL-8) are secreted by corneal cells after infection with HSV-1. Both CXCL-2 and IL-8 are potent chemo-attractants for PMN. PMN are the predominant inflammatory cells in the infiltrate of the cornea the first days after infection with HSV -1, and are involved in the elimination of infectious virus of the eye. Therefore, Compound 1 would favor the secretion of cytokines and chemokines that stimulate the recruitment of PMN after infection with HSV-1.

We further noted the overexpression of macrophage colony stimulating factor (CSF-2) in infected HCLE cells treated with Compound 1, with respect to untreated infected controls (Table 1). CSF-2 is one of the key regulators of the effector function of both mature neutrophil and macrophages. It delays apoptosis of these cells and induces the release of proteolytic enzymes and oxygen free radicals in them.

Therefore, the pro-inflammatory effect of Compound 1 observed in vitro would be eliciting the innate immune response responsible for viral clearance in vivo.

On the other hand, there was an overexpression of genes for IL-12, IL-23 and CXCL10, in LPS-stimulated macrophages treated with Compound 1, compared to untreated stimulated macrophages (Table 1). It has been shown that IL-12 directly inhibits angiogenesis or does so indirectly, through the induction of IFN-α, which, in turn, activates CXCL10, with a well-known antiangiogenic activity. IL-12 and IL-23 have one of their subunits in common, IL-12, p40 or IL-12b. IL-23 uses many of the same signal-transduction components as IL-12. This may explain the similar actions of IL-12 and IL-23 in promoting cellular immunity and proliferative responses in target cells. In LPS-stimulated cells treated with Compound 1, the expression of both IL-10 as Socs2 was also increased compared to the untreated control (Table 1). Socs2 protein is an anti-inflammatory mediator that blocks NF-κB and JAK-STAT pathways, thereby inhibiting the release of pro-inflammatory cytokines such as TNF-α, IL-6 and IL-8. IL-10 by itself exhibits anti-inflammatory properties, and one of its effects is the induction of Socs2 protein expression.

Moreover, both ATF3 and TLR4 were overexpressed in J774A.1 cells stimulated with LPS and treated with Compound 1 (Table 1). ATF3 displays an anti-inflammatory role. This factor is activated via TLR4 and then inhibits gene induction stimulated by the same TLRs.

ATF3 intervenes as a negative regulator of the inflammatory response in macrophages by antagonizing NF-κB induced responses.

Dusp2 gene expression was also restrained after the treatment of LPS-activated macrophages with Compound 1 (Table 1). It is well known that the family of DUSP proteins regulates the activity of MAPKs, critical in triggering the inflammatory response and cellular immune function. While DUSP are phosphatases that inactivate MAPK, it has been shown that the absence of Dusp2 expression causes a decrease in the production of pro-inflammatory cytokines.

Hence, Compound 1 would be inhibiting pro-inflammatory factors and stimulating anti-inflammatory molecules in macrophages activated with a non-viral stimulus, suggesting an immunosuppressive action over inflammatory cells.

In conclusion, Compound 1 exerts an immunomodulatory activity depending upon the cell type involved. In the case of HSV-1-infected HCLE cells, the compound does not affect TNF-α and IL-6 levels and induces an increase in the amount of IL-8. By contrast, the stigmastane causes a drop in cytokine quantities in LPS-activated macrophages.

Through microarray assays, we confirmed the inhibitory effect of Compound 1 on activated inflammatory cells, which lacks in the case of treated-infected cells. Furthermore, Compound 1 displayed an immunostimulatory activity in HSV-1-infected epithelial cells.

4. Compound 1 Affects VEGF Expression

IL-6 is a potent angiogenic agent that exerts its action by stimulating the production of VEGF, the major growth factor responsible for angiogenesis and, in certain cases, an important mediator of pathological angiogenesis processes.

In the case of HSK, IL-6 produced by non-infected corneal cells first, and later by inflammatory cells, would lead the secretion of VEGF in the infected corneas.

Nevertheless, the main source of VEGF is not the infected cells, but uninfected ones adjacent to them. On the other hand, when corneas of mice infected with HSV-1 are treated with VEGF antagonists, a partial but significant reduction of angiogenesis, as well as the incidence and severity of the lesions of keratitis are observed.

Since Compound 1 decreased the incidence and severity of neovascularization in mice infected corneas treated from day 1 p.i. onwards, and also when administered at the onset of disease, at 6 days p.i. (data not shown), we studied if the stigmastane exerted any effect on the secretion of VEGF.

For that purpose, J774A.1 cells were transfected with a VEGF reporter plasmid LUC and a plasmid β-galactosidase (β-gal) as a control of transfection.

Since we had observed that stimulation of J774A.1 cells with LPS resulted in an increased secretion of IL-6 (FIG. 3G), we decided to induce the expression of VEGF-LUC in J774A.1 cells with the direct stimulus of IL-6 and the indirect stimulation of LPS. The higher levels of VEGF expression were detected after 8 h and 16 h of stimulation with LPS and IL-6, respectively.

Thus, J774A.1 cells grown in 6-well microplates were transfected with plasmids pVEGF-LUC and pβ-gal. At 24 h post-transfection, cells were stimulated with 100 ng/ml of LPS and ng/ml of IL-6, in the absence and presence of 40 mM of Compound 1. Then, we measured the expression of VEGF and β-gal in the harvested samples and determined the expression of luciferase as a reporter of VEGF promoter activity, by normalizing the values obtained with those of β-gal activity. In the absence of stimuli, J774A.1 cells exhibited a baseline expression of VEGF/β-gal of 13307.5±3372.3. Compound 1 alone did not induce the expression of VEGF, since no significant differences between its baseline expression and that obtained in the presence of the compound were observed (FIG. 4).

When cells were stimulated either with LPS or IL-6, a significant raise in VEGF expression with respect to non-stimulated controls was observed (93201.5±26770.4, $p<0.1$, and 30929.5±5464, $p<0.05$, respectively). In both cases, Compound 1 was effective in lessening considerably VEGF expression, since it dropped to 22098.5±4052.4 ($p<0.1$) and 17900±2689.7 ($p<0.05$) after induction with LPS and IL-6, correspondingly.

5. Compound 1 Intervenes in Capillary Tube Formation and Cell Invasion In Vitro

Considering that VEGF synthesis was restrained by Compound 1 and the tube formation of endothelial cells is a key step along the angiogenic process, a capillary tube formation assay to test the anti-angiogenic effect of the stigmastane in a cellular system was performed. The Matrigel assay condition supported differentiation of untreated HUVECs into an extensive and complete network of capillary-like structures (FIG. 5). The capillary tube-like network was slightly inhibited at the lowest doses of Compound 1, since 2.5 and 5 µM reduced the tube formation in 17.3% and 25.9% with respect to untreated control (FIGS. 5A, B and C).

Although these values were not statistically significant, treatment with higher doses of Compound 1 (10 µM and 20 µM) evidenced fragments of unconnected tubes, which led to a 59.8% and 90.7% reduction of the tube-like network ($p<0.01$), respectively (FIGS. 5D and E). In this sense, a dose-response profile was obtained, since 40 µM of the stigmastane inhibited in 93.9% the tube formation ($p<0.001$) whereas a complete inhibition with 50 and 100 µM was observed (FIGS. 5F, G and H).

As endothelial cell invasion is a critical and initiating event in angiogenesis, the ability of HUVECs to migrate through a porous membrane was assessed. Twenty-four h after cell seeding, we counted the number of invading cells and found that 100 ng/ml of IL-6 significantly enhanced cell invasion through the filter membrane in 155% ($p<0.001$). Compound 1 efficiently suppressed HUVECs invasion through the filter in a concentration dependent manner because a 67.5%, 26.1% and 18.4% inhibition at 40 µM, 20 µM and 10 µM, respectively, was achieved ($p<0.001$).

Discussion

Many viral infections result in clinically relevant immunological diseases. The treatment of these immunopathologies is usually done through the administration to the patient of immunosuppressants such as corticosteroids. However, these treatments can result in the prolongation of the disease due to reactivation of the virus which persists in the host cells, as in the case of HSK.

HSK is an immunopathology of viral origin in which the lesions observed in the eye are not caused by viral replication per se, but as a consequence of the inflammatory response triggered by viral replication. Ocular lesions become evident when the virus is no longer detectable in the eye. Guess et al. (2007) discuss the need of administration of an antiviral like ACV together with corticosteroids, for the treatment of HSK in humans, so as to mitigate the possible viral reactivation due to immunosuppression caused by anti-inflammatory drugs.

However, the availability of anti-herpetic drugs is scarce, and the use of commonly used antiviral drugs against HSV-1 is limited by the emergence of viral mutants resistant to these drugs. This fact coupled with the absence of a prophylactic vaccine for HSV-1, raises the need to search for new drugs effective against this virus.

From our results on the effect of Compound 1 in the eyes of HSV-1 infected mice, the fact that attracts most our attention is that, even in the absence of an antiviral effect of the stigmastane under the experimental conditions previously reported, it manages to reduce significantly the signs of disease that develop later in the corneas. Since the healing effect of the compound is not due to a direct antiviral action and is observed several days after the end of treatment, it is likely that the improvement of HSK observed is related to a modulatory activity of Compound 1 on the innate immune response once the infection is established. HSV-1 infection induces NF-κB activation and the secretion of pro-inflammatory cytokines such as TNF-α and IL-6. NF-κB activation occurs in two phases: the first one, rapid and transient, could be induced by the interaction of viral gD with receptors HVEA in the host cell and, therefore, would be independent of viral replication; a second phase of activation, sustained over time, requires active viral replication and viral protein synthesis.

Compound 1 was added to the cells after infection with HSV-1, which was not present during the outbreak of the first wave of activation of NF-κB. Compound 1 blocked NF-κB activation at 24 h p.i., so it inhibited the second phase of NF-κB activation. This would be the consequence of its inhibitory activity on HSV-1 replication in vitro. The compound did not inhibit NF-κB translocation, but reduced viral replication and with it, the number of infected cells in which NF-κB nuclear translocation had occurred.

During infection with HSV-1, increased levels of IL-6 in the eye favor the arrival of inflammatory cells, such as neutrophils and macrophages, responsible for virus elimination from the cornea.

Infected epithelial cells treated with Compound 1 did not suffer a reduction in IL-6 levels unlike DEX which, due to its known immunosuppressive action, produced a significant inhibition of this cytokine secretion in infected cells (FIGS. 2B and C). The effect of Compound 1 on IL-6 yield seems to be contradictory with its inhibitory effect on NF-κB translocation (FIGS. 1B and E). However, we hypothesized that this effect was the result of a balance between the inhibitory activity of the stigmastane on NF-κB activation and an inhibitory effect on the destabilizing action exerted by ICP4 and ICP27 viral proteins on cytokines coding mRNA, a consequence of its antiviral activity in vitro.

Figure 2:
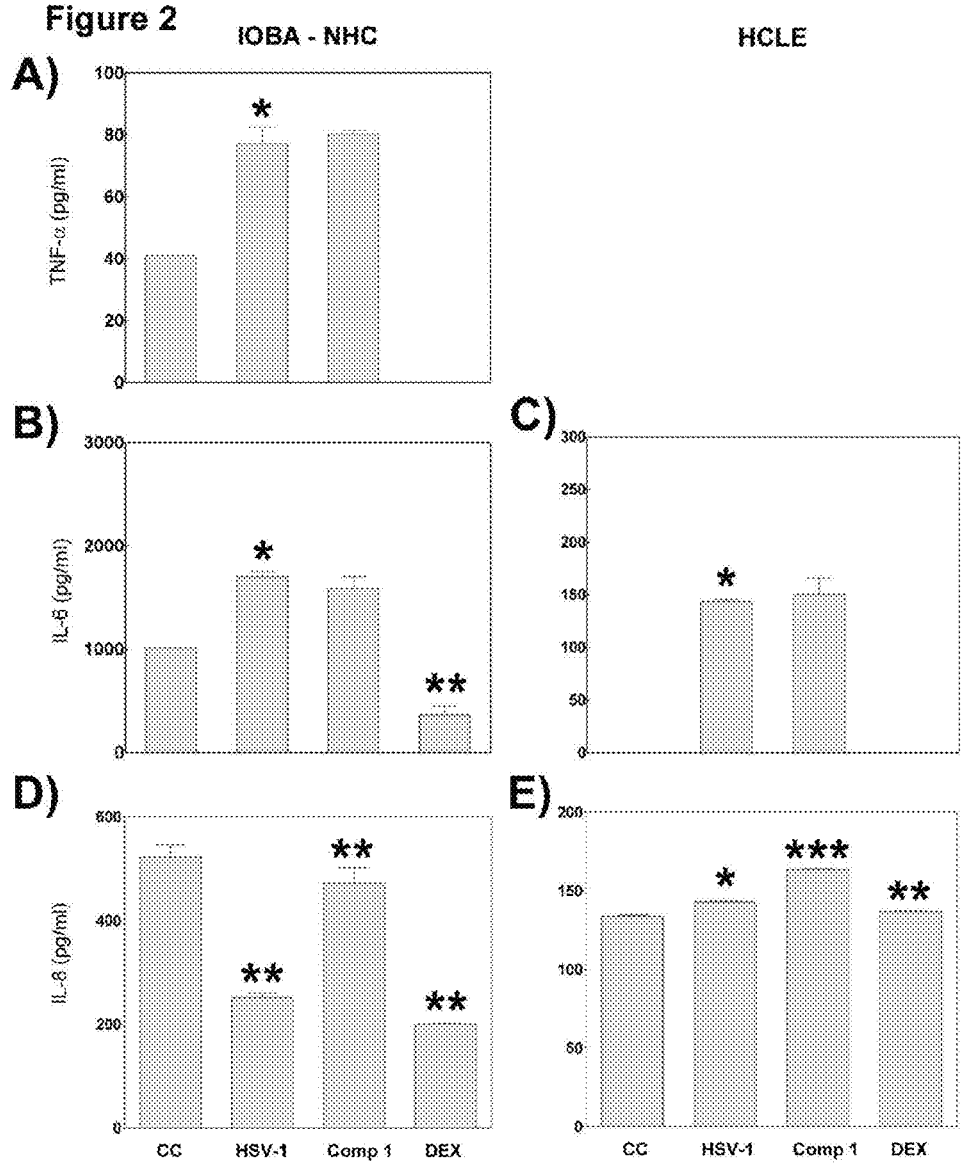
FIG. 2. Effect of Compound 1 on the secretion of TNF-α, IL-6 and IL-8 in epithelial cells. (A, B and D) IOBA-NHC and (C and E) HCLE cells infected with HSV-1 (m.o.i.=1) were treated or not with 40 μM of Compound 1 or DEX. After 24 h, TNF-α, IL-6 and IL-8 were quantified by ELISA in cell supernatants. * p<0.01, with respect to untreated infected cells and to untreated uninfected cells; p<0.001, with respect to untreated infected cells and to untreated uninfected cells, *p<0.00001, with respect to untreated infected cells and to untreated uninfected cells.

The high levels of pro-inflammatory cytokines such as TNF-α, IL-6 and IL-8 in HCLE and IOBA-NHC infected cells treated with the stigmastane is a differential characteristic with respect to DEX, which induced a reduction in the levels of these cytokines in both cell lines (FIG. 2).

Therefore, although Compound 1 had shown no antiviral activity in vivo, it could be exerting a modulating effect on the expression of inflammatory mediators induced by the virus in infected cells or non infected cells neighboring the infected ones, which could explain the differences found between the eyes of animals treated with the stigmastane and those treated with DEX during the first days p.i., when the virus was not completely eliminated.

On the other hand, Compound 1 restrained the production of pro-inflammatory cytokines TNF-α and IL-6 in LPS-induced macrophages (FIG. 3G). Thus, the ability of these cells to eliminate the virus from the eyes of HSV-1 infected mice would be restricted by Compound 1 that, in turn, would account for a reduced power of these cells to cause damage to the infected corneas.

Our results strongly suggest that Compound 1 would exert an immunosuppressive action on inflammatory cells taking part in the innate immune response displayed during HSK, in the same way DEX does, but the stigmastane would have a different effect on infected epithelial cells (FIGS. 2 and 3).

Compound 1 proved to diminish VEGF expression when induced by two different stimuli, LPS and IL-6, which led not only the tube-like formation in endothelial cells but also migration of these cells, two major events during angiogenesis (FIGS. 4 and 5). This property gives Compound 1 an advantage over other compounds of the kind, given that some other synthetic molecules that belong to the family of Compound 1, with in vitro antiviral and immunomodulatory activity, do not have an antiangiogenic activity in the tube-like formation assay in HUVEC cells.

Thus, Compound 1 proved to exert an anti-angiogenic effect—besides the antiviral and immunomodulating properties already described—and, hence, the healing of murine HSK would also be due to an anti-angiogenic action of Compound 1 against the neovascularization process of the cornea during HSV-1 induced ocular disease. This novel effect of Compound 1 is not shared with other compounds belonging to the same family of synthetic analogs with antiviral and immunomodulating properties. Therefore, we can conclude that the anti-angiogenic effect of Compound 1 is not a consequence of its immunomodulating activity.

In summary, the synthetic stigmastane designed as Compound 1 would be a promising compound not only to cure an immunopathology of viral origin like HSK, but also to improve other diseases where angiogenesis is the major pathogenic factor as in case of solid tumor.

Method of Obtaining Compound 2:

(22S,23S)-22,23-dihydroxystigmasta-1,4-dien-3-one 120 mg of (22S,23S)-22,23-dihydroxystigmast-4-en-3-one are dissolved in 15 mL dioxane anhydrous. 180 mg of 2,3-dichlorine-5,6-diciano-1,4-benzoquinone (DDQ) are added and the mixture is refluxed, with stirring and inert atmosphere, during 24 hours.

The resulting suspension is filtrated and the filtrate evaporated to dryness. The resulting crude product is purified by silica column chromatography (eluting solvent: hexane/ethyl acetate 1:1). 87 mg of (22S,23S)-22,23-dihydroxystigmasta-1, 4-dien-3-one are obtained.

$^1$H-RMN (CDCl$_3$, 200 MHz): 6.50 (1H, d, J=10 Hz, H-1); 5.93 (1H, d, J=10 Hz, H-2); 5.80 (1H, s, H-4); 3.61 (2H, m, H-22 and H-23 )

$^{13}$C-RMN (CDCl$_3$, 50 MHz): 186.0 (C-3); 168.4 (C-5); 155.3 (C-1 ); 127.4 (C-2); 123.8 (C-4); 72.3 (C-22); 70.7 (C-23). IR: 3300 and 1665 cm$^{-1}$ Evaluation of the Antiangiogenic Activity of the Compound 1 and Compound 2, and Other Brassinosteroids (Compound III and Compound IV)

It was performed a capillary tube formation assay to evaluate a possible anti-angiogenic effect of Compound 2, in comparison with another brassinosteroids.

Compound 2 comprises the compound (22S,23S)-22,23-dihydroxystigmasta-1,4-dien-3-one which is obtained by reduction of Compound 1 introducing a Δ$^1$ doublebond.

Compounds III and IV have similar structure than Compound 1 and Compound 2 respectively, with the addition of a fluorine atom (F) in position 6 of the steroid structure.

The structural formulas of the compounds studied 1, 2, III and IV are the following:

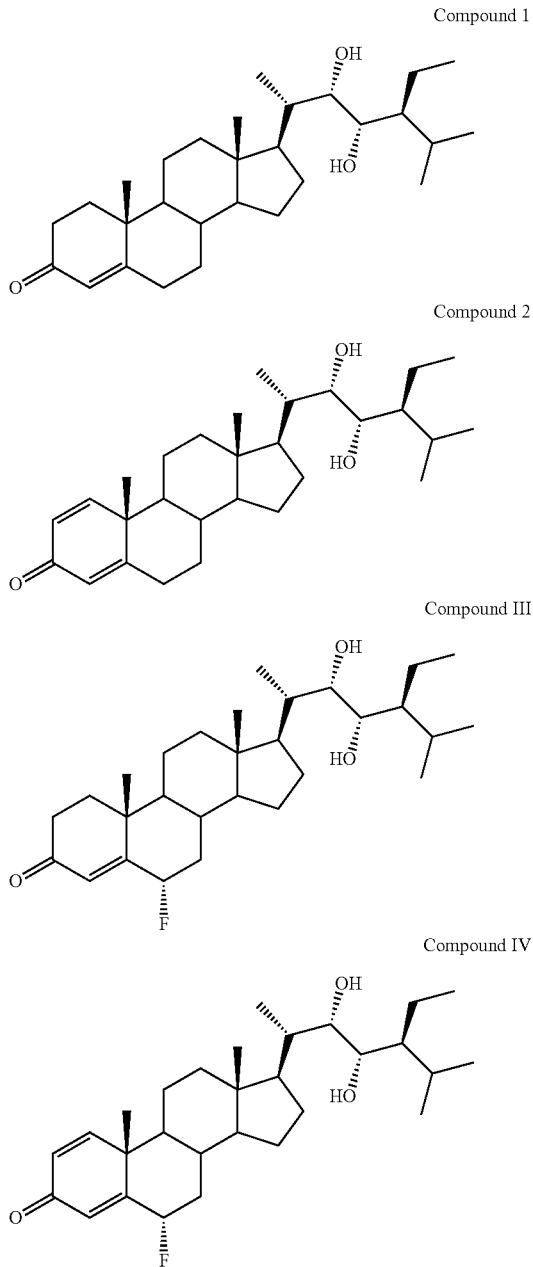

Compound 1

Compound 2

Compound III

Compound IV

The four compounds were able to inhibit the production of TNF-α in macrophages stimulated with LPS, ie all exhibit immunomodulatory activity.

The formation of capillary tube-like structures by HUVEC cells was analyzed on 24-well cell culture plates coated with an extracellular membrane matrix (Matrigel; BD Biosciences). Matrigel was thawed at 4° C. Using precooled plates and tips, 100 μl/well of Matrigel was distributed and allowed to gelify at 37° C. for at least 30 min. Cells were seeded on the polymerized Matrigel (5 to $8 \times 10^4$ cells/well) in absence and presence of concentrations of 20 μM and 40 μM of each compound. The plate was incubated at 37° C., and tube formation was observed under an optic inverted microscope. Compound 1 was used as positive control.

Compounds 1, 2, III and IV belong to the family of compounds covered by international and national patent P070103089 PCT/IB2008/052703.

Compound 2 (as compound 1 in before assays) showed inhibitory activity of capillary tube like structures in both concentrations evaluated. On the contrary, in presence of compounds III and IV, HUVEC cells develop the formation of capillary tube-like structures in same manner than control cells without treatment.

Despite having compounds III and IV structural characteristics and immunomodulatory capacity similar to compounds 1 and 2, antiangiogenic activity is not present in compounds III and IV.

Compositions of Brassinosteroids of General Formula (I):

In one embodiment of the invention, a formulation for treating of solid tumor selected from the group consisting of breast carcinoma, lung carcinoma, prostate carcinoma, colon carcinoma, ovarian carcinoma, neuroblastoma, central nervous system tumor, multiform glioblastoma and melanoma comprises (a) brassinosteroids of general formula (I)

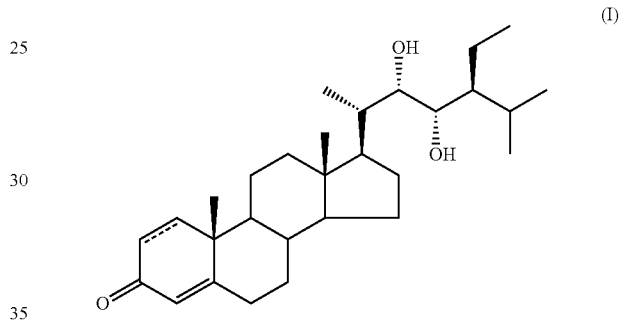

(I)

wherein ⚍ can be a single or double bond and the configurations of carbon atoms C22 and C23 respectively linked to the substituents HO are S for both carbon atoms, and a pharmaceutically acceptable additive, the pharmaceutically acceptable additive being a component selected from carrier, binding agent, stabilizer, adjuvant, diluent, excipient, surfactant, odorant, or dye.

In other embodiment of the invention, a formulation for treating of solid tumor selected from the group consisting of breast carcinoma, lung carcinoma, prostate carcinoma, colon carcinoma, ovarian carcinoma, neuroblastoma, central nervous system tumor, multiform glioblastoma and melanoma comprises (22S,23S)-22,23-dihydroxystigmast-4-en-3-one (Compound 1), and pharmaceutically acceptable additive, the pharmaceutically acceptable additive being a component selected from carrier, binding agent, stabilizer, adjuvant, diluent, excipient, surfactant, odorant, or dye. In other embodiment of the invention, a formulation for treating of solid tumor selected from the group consisting of breast carcinoma, lung carcinoma, prostate carcinoma, colon carcinoma, ovarian carcinoma, neuroblastoma, central nervous system tumor, multiform glioblastoma and melanoma comprises (22S,23S)-22,23-dihydroxystigmasta-1,4-dien-3-one (Compound 2), and an additive, the additive being a component selected from carrier, binding agent, stabilizer, adjuvant, diluent, excipient, surfactant, odorant, or dye. A formulation according to the invention may further comprise a second pharmaceutically active agent selected from antiviral, antifungal, antibacterial, antiseptic, anti-inflammatory, immunomodulatory, antineoplastic, anti-angiogenic and analgesic agents.

In said formulation the anti-angiogenic agent is selected from the group consisting of vincristine, vinblastine, vinorelbine, vindesine, paclitaxel, docetaxel, 5 FU, cisplatin, carboplatin, irinotecan, topotecan and cyclophosphamide.

The composition according to the invention, comprising brassinosteroids of general formula (I) as active ingredient, which is administered, in a preferred embodiment, orally, for example, as tablets or lozenges or capsules, in suspensions or emulsions, or in solutions, in powders or granules, or in syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically acceptable preparations. The tablets may be uncoated or they may be coated by known techniques to delay disintegration and absorption. A composition comprising a brassinosteroid general formula (I) may be employed as a food additive. A low toxicity of brassinosteroids enables to employ safely sufficiently high therapeutic doses. For example, daily oral doses, for an adult subject, may comprise from about 10 ug to about 1000 mg of brassinosteroid of general formula (I).

In a method according to the invention, brassinosteroids general formula (I), may be administered orally or parenterally. For example, a composition comprising brassinosteroids general formula (I) may be administered intramuscularly, intraperitoneally, or intravenously. In one embodiment, the active formulation may be inserted to the body of a subject in need of the treatment by subcutaneous injection. On other embodiment, a deposit or an implant is inserted into the body, providing a slow release of brassinosteroids general formula (I) in the body. The brassinosteroids (22S,23S)-22,23-dihydroxystigmast-4-en-3-one (Compound 1) and (22S,23S)-22,23-dihydroxystigmasta-1,4-dien-3-one (Compound 2) were formulated as the following suspension:

| Compound 1 or 2: | 1 mg |
|---|---|
| Sodium sulfate | 36.0 mg |
| Sodiun Chloride | 9.0 mg |
| EDTA | 0.3 mg |
| Hydroxyethylcellulose | 10.0 mg |
| Tyloxapol | 1.5 mg |
| Distilled water | 3 mL |

The resulting pharmaceutical composition can be used by parenteral route.

Evaluation of the Effect of Compound 1 Over the Angiogenic Response of the Murine Breast Tumoral Cell Line LMM3 in Balb/C Mice.

Introduction

The tumoral angiogenesis is a fundamental process that comprises the formation of new blood vessels which facilitates the intake of oxygen and nutrients by the tumor promoting its growth and metastasis.

Previous to the in vivo assay, the potential cytotoxic effect of Compound 1 was evaluated at different concentrations over the LMM3 breast tumor cell line and the normal cell line NMuNG. This measure ensures that the Compound 1, in the concentrations used in the in vivo assay, are acting over the angiogenic process, which is previous to the growth of the tumoral mass and that it has no effect over normal cells of the same lineage. The cytotoxic effect of Compound 1 was evaluated as a dose-response curve and each concentration was evaluated at 2 different times. From this assay the effective concentration of Compound 1 to be used in the in vivo assay was selected. Said concentration was 0.025 µg/µl.

Scope

To evaluate the capacity of Compound 1 to exert an anti-angiogenic effect in an in vivo neovascularization model.

Methods

For the in vivo assay, $2 \times 10^6$ cells/mL were grown in 1 mL of complete medium in 6 wells plates. Compound 1 was incubated with LMM3 cells during 1 h and 6 hs. Also, a group of non-treated tumoral cells were grown and incubated. Then, all the cells from each group were washed with PBS, trypsinized and re-suspended in 0.9 ml of F12 medium without FBS.

Female BALB/c mice were randomized as follows:
Sham N=4
LMM3 N=4
LMM3+Compound 1-1 hour treatment N=4
LMM3+Compound 1-6 hours treatment N=4

Then, inoculation of $2 \times 10^5$ cells/0.1 mL was done intradermically in the mouse flanks. After 5 days the animals were sacrificed and photographs of the inoculation site were taken.

The vessels density was quantified in each animal and the results were analized by ANOVA followed by the Tukey test. Results were expressed as the median of vessels density (vessels/mm$^2$+/−ES).

Results

In FIG. 6 it can be seen that, as previously described (Davel LE, 2004; Bueno Calif., 2012), the inoculation of LMM3 cells increases the neovascular response in the injection site compared to the "Sham" group (control inoculated with vehicle only). The pre-incubation of the cells with Compound 0.025 µg/µl during 1 h and 6 h significantly reduced the angiogenic response induced by LMM3 cells, decreasing the quantified density of vessels to values similar to the ones shown by the group "Sham".

The results obtained with Compound 1 in the described assay show the antiangiogenic effect of the compound over the tumoral cell line LMM3 and indicate that it has the capacity of significantly reducing the tumoral angiogenesis in BALB/c mice.

Bibliography

Davel L E, Rimmaudo L, Espanol A, de la Torre E, Jasnis M A, Ribeiro M L, Gotoh T, de Lustig E S, Sales M E. Different mechanisms lead to the angiogenic process induced by three adenocarcinoma cell lines. Angiogenesis. 2004; 7(1):45-51.

Bueno C A, Lombardi M G, Sales M E, AlchéL E. A natural antiviral and immunomodulatory compound with antiangiogenic properties. Microvasc. Res. 2012 November; 84(3): 235-41.

Final Conclusion

Besides its ability of modulating the immune response to viral and non viral stimuli, Compound 1 behaves as an anti-angiogenic drug. In vitro, it proved to diminish VEGF expression when induced by two different stimuli, LPS and IL-6, and significantly impeded not only the tube-like formation in endothelial cells but also migration of these cells, two major events occurring during angiogenesis (see FIGS. 4 and 5). In vivo, Compound 1 significantly reduces the tumoral angiogenesis in BALB/c mice too.

The antiangiogenic effect described places Compound 1 in advantage over other compounds of the same family of synthetic analogs, given that some of them, with in vitro antiviral and immunomodulatory activities, do not have an antiangiogenic activity in the tube-like formation assay in HUVEC cells. Thus, the antiangiogenic activity of Compound 1 displayed in vitro and in vivo is not a consequence of their immunomodulatory properties. The novel antiangiogenic activity of Compound 1 would be associated with the lack of neovascularization in the cornea of mice during HSV-1-induced ocular disease.

In summary, the synthetic stigmastane designed as Compound 1 would be a promising compound not only to cure an immunopathology of viral origin like HSK, but also to improve other diseases where angiogenesis is the major pathogenic factor as i.e. for inhibiting of angiogenesis in a mammal which has a solid tumor selected from the group consisting of breast carcinoma, lung carcinoma, prostate carcinoma, colon carcinoma, ovarian carcinoma, neuroblastoma, central nervous system tumor, multiform glioblastoma and melanoma.

The invention claimed is:

1. A method of treating a solid tumor in a mammal by inhibiting angiogenesis, comprising administering to a mammal in need thereof a composition comprising
an effective amount of a brassinosteroid of general formula (I)

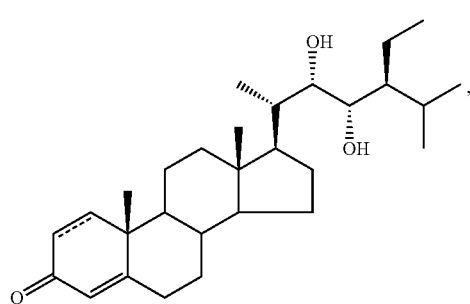

wherein ⚏ is a single bond or a double bond, and both carbon atoms C22 and C23 respectively linked to the OH substituents have the S configuration, and
a pharmaceutically acceptable additive,
wherein the solid tumor is selected from the group consisting of breast carcinoma, lung carcinoma, prostate carcinoma, colon carcinoma, ovarian carcinoma, neuroblastoma, central nervous system tumor, multiform glioblastoma and melanoma.

2. The method according to claim 1, wherein the brassinosteroid of general formula (I) is
(22S,23S)-22,23-dihydroxystigmast-4-en-3-one, or
(22S,23S)-22,23-dihydroxystigmasta-1,4-dien-3-one.

3. The method according to claim 2, wherein the pharmaceutically acceptable additive is one or more selected from carrier, binding agent, stabilizer, adjuvant, diluent, excipient, surfactant, odorant, and dye.

4. The method according to claim 1, wherein the pharmaceutically acceptable additive is one or more selected from carrier, binding agent, stabilizer, adjuvant, diluent, excipient, surfactant, odorant, and dye.

5. The method according to claim 1, wherein the composition further comprises a second pharmaceutically active agent selected from antiviral, antifungal, antibacterial, antiseptic, anti-inflammatory or immunomodulatory, antineoplastic, anti-angiogenic, and analgesic compounds.

6. The method according to claim 5, wherein the anti-angiogenic agent is selected from the group consisting of vincristine, vinblastine, vinorelbine, vindesine, paclitaxel, docetaxel, 5 FU, cisplatin, carboplatin, irinotecan, topotecan, and cyclophosphamide.

7. A composition for treating a solid tumor in a mammal by inhibiting angiogenesis, the composition comprising a brassinosteroids of general formula (I)

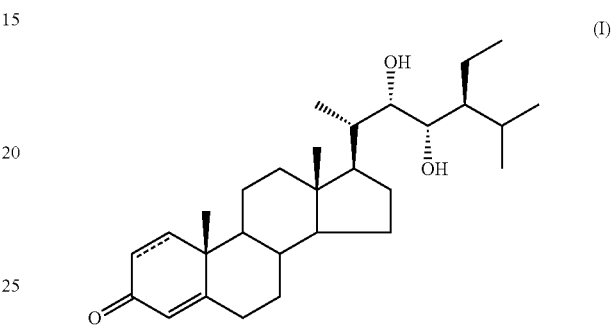

wherein ⚏ is a single bond or a double bond, and both carbon atoms C22 and C23 respectively linked to the OH substituents have the S configuration, and
wherein the solid tumor is selected from the group consisting of breast carcinoma, lung carcinoma, prostate carcinoma, colon carcinoma, ovarian carcinoma, neuroblastoma, central nervous system tumor, multiform glioblastoma, and melanoma.

8. The composition according to claim 7, wherein the brassinosteroid of general formula (I) is
(22S,23S)-22,23-dihydroxystigmast-4-en-3-one, or
(22S,23S)-22,23-dihydroxystigmasta-1,4-dien-3-one.

9. The composition according to claim 7, further comprising a pharmaceutically acceptable additive.

10. The composition according to claim 9, wherein the pharmaceutically acceptable additive is one or more selected from carrier, binding agent, stabilizer, adjuvant, diluent, excipient, surfactant, odorant, and dye.

11. The composition according to claim 7, wherein the composition further comprises a second pharmaceutically active agent selected from antiviral, antifungal, antibacterial, antiseptic, anti-inflammatory or immunomodulatory, antineoplastic, anti-angiogenic, and analgesic compounds.

12. The composition according to claim 11, wherein the anti-angiogenic agent is selected from the group consisting of vincristine, vinblastine, vinorelbine, vindesine, paclitaxel, docetaxel, 5 FU, cisplatin, carboplatin, irinotecan, topotecan, and cyclophosphamide.

* * * * *